United States Patent [19]

Bornzin et al.

[11] Patent Number: 5,549,650
[45] Date of Patent: Aug. 27, 1996

[54] SYSTEM AND METHOD FOR PROVIDING HEMODYNAMICALLY OPTIMAL PACING THERAPY

[75] Inventors: Gene A. Bornzin, Camarillo; Kelly H. McClure, Simi Valley; Gabriel Mouchawar, Newhall; Sheldon B. Moberg, Kagel Canyon, all of Calif.

[73] Assignee: Pacesetter, Inc., Sylmar, Calif.

[21] Appl. No.: 259,084

[22] Filed: Jun. 13, 1994

[51] Int. Cl.$^6$ .................................................. A61N 1/365
[52] U.S. Cl. ................................................ 607/24; 607/25
[58] Field of Search ........................... 607/17–19, 24–25, 607/9

[56] References Cited

U.S. PATENT DOCUMENTS

| | | | |
|---|---|---|---|
| 3,554,199 | 1/1971 | Auphan | 607/19 |
| 4,917,115 | 4/1990 | Flammang et al. | 607/19 |
| 5,109,842 | 5/1992 | Adinolfi | 607/2 |
| 5,156,147 | 10/1992 | Warren et al. | 607/24 |
| 5,304,208 | 4/1994 | Inguaggiato et al. | 607/17 |
| 5,423,883 | 6/1995 | Helland | 607/18 X |

OTHER PUBLICATIONS

I. Ovsyshcher et al., "First Derivative of Right Ventricular Pressure dP/dt, as a Sensor for a Rate Adaptive VVI Pacemaker: Initial Experience," *Pace*, vol. 15, Feb. 1992, pp. 211–218.

*Primary Examiner*—William E. Kamm
*Assistant Examiner*—Jeffrey R. Jastrzab
*Attorney, Agent, or Firm*—Lisa P. Weinberg

[57] ABSTRACT

A system and method for a pacemaker are provided, for using cardiac wall motion sensor signals to provide hemodynamically optimal pacing therapy to patient at rest, and for providing rate-responsive pacing therapy. The cardiac wall motion sensor signals are provided by an implantable lead that incorporates an accelerometer for measuring cardiac mechanical activity. The cardiac wall motion sensor signals are processed to derive cardiac wall velocity signals and cardiac wall displacement signals. The derived signals are further processed to derive physiologic parameters indicative of cardiac performance, including stroke volume, contractility, pre-ejection period, and ejection time. The physiological parameters, in turn, are used by the pacemaker to provide hemodynamically optimal pacing therapy at rest, and rate-responsive pacing therapy.

26 Claims, 7 Drawing Sheets

SYSTEM AND METHOD FOR PROVIDING HEMODYNAMICALLY OPTIMAL PACING THERAPY

BACKGROUND OF THE INVENTION

This invention relates to implantable cardiac stimulating devices and particularly to implantable cardiac pacemakers which use implantable leads. More particularly, this invention relates to a system and method for providing hemodynamically optimal pacing therapy to a patient while the patient is at rest and for providing hemodynamically optimal rate-responsive pacing therapy.

A pacemaker is an implantable medical device which delivers electrical stimulation pulses to cardiac tissue to relieve symptoms associated with bradycardia—a condition in which a patient cannot normally maintain a physiologically acceptable heart rate. Early pacemakers delivered stimulation pulses at regular intervals in order to maintain a predetermined heart rate—typically a rate deemed to be appropriate for the patient at rest. The predetermined rate was usually set at the time the pacemaker was implanted, although in more advanced pacemakers, the rate could be set remotely after implantation.

Early advances in pacemaker technology included the ability to sense the patient's natural cardiac rhythm (i.e., the patient's intracardiac electrogram, or "IEGM"). This led to the development of "demand pacemakers"—so named because they deliver stimulation pulses only as needed by the heart. Demand pacemakers are capable of detecting a spontaneous, cardiac depolarization which occurs within a predetermined time period (commonly referred to as the "escape interval") following a preceding depolarization. When a naturally occurring depolarization is detected within the escape interval, the demand pacemaker does not deliver a pacing pulse. The ability of demand pacemakers to avoid delivery of unnecessary stimulation pulses is desirable because by doing so, battery life is extended. Furthermore, stimulation in the heart's vulnerable period during the T-wave is avoided, which is otherwise known to cause fibrillation.

Modern pacemakers allow physicians to telemetrically adjust the length of the escape interval, which has the effect of altering the heart rate maintained by the device. However, in early devices, this flexibility only allowed for adjustments to a fixed programmed rate, and did not accommodate patients who required increased or decreased heart rates to meet changing physiological requirements during periods of elevated or reduced physical activity. Therefore, unlike a person with a properly functioning heart, a patient receiving therapy from an early demand pacemaker was paced at a constant heart rate—regardless of the level to which the patient was engaged in physical activity. Thus, during periods of elevated physical activity, the patient was subject to adverse physiological consequences, including lightheadedness and episodes of fainting, because the heart rate was forced by the pacemaker to remain constant.

The adverse effects of constant rate pacing lead to the development of "rate-responsive pacemakers" which can automatically adjust the patient's heart rate in accordance with metabolic demands. An implanted rate-responsive pacemaker typically operates to maintain a predetermined minimum heart rate when the patient's level of metabolic need is at or below a threshold level, and gradually increases the maintained heart rate in accordance with increases in metabolic need until a maximum rate is reached. Rate-responsive pacemakers typically include processing and control circuitry that correlates a physiological parameter indicative of metabolic need to a desirable heart rate. In many rate-responsive pacemakers, the minimum heart rate, maximum heart rate, and the transition rates between the minimum heart rate and the maximum heart rate are parameters that may be adjusted to meet the needs of a particular patient.

One approach that has been considered for enabling rate-responsive pacemakers to determine an appropriate heart rate involves measuring a physiological parameter that reflects the level to which the patient is engaged in physical activity. Physiological parameters that have been considered include central venous blood temperature, blood pH level, QT time interval and respiration rate. However, certain drawbacks (such as slow response time, unpredictable emotionally-induced variations, and wide variability across individuals) render the use of these physiological parameters difficult, and accordingly, they have not been widely used in practice.

Rather, most rate-responsive pacemakers employ sensors that transduce mechanical forces associated with physical activity. These activity sensors generally contain a piezoelectric transducing element which generates a measurable electrical potential when a mechanical stress resulting from physical activity is experienced by the sensor. By analyzing the signal from a piezoelectric activity sensor, a rate-responsive pacemaker can determine how frequently pacing pulses should be applied to the patient's heart.

Some rate-responsive pacemakers monitor physiologic parameters, other than the IEGM, which reflect hemodynamic performance. For example, U.S. Pat. No. 4,774,950 of Cohen refers to a system that measures mean pressure at a variety of locations (e.g., mean arterial pressure, mean right ventricular pressure, mean left atrial pressure, mean left ventricular pressure or mean central venous pressure). For a selected mean pressure, a short term current mean pressure is compared to a long term mean baseline pressure. The mean pressure data may be used as a hemodynamic indicator to infer stroke volume by taking pressure-time histories of arterial blood flow. The inferred stroke volume may be used to control the rate of pacing.

The use of another hemodynamic indicator in rate-responsive pacing, blood oxygen level, is described in U.S. Pat. No. 4,967,748 of Cohen. Blood oxygen level is measured at a particular site in the circulatory system of a patient. The blood oxygen level measurements may be used to control the rate of pacing by altering the stimulating frequency of an associated pacemaker.

Another example of using pressure as a hemodynamic indicator in rate-responsive pacing is described in U.S. Pat. No. 4,708,143 of Schroeppel. That patent describes the use of a pressure sensor to sense the opening and closure of the tricuspid valve, the sensed opening and closure being used to determine ejection time. The changes in ejection time are processed to determine a corresponding change in stroke volume that is used to adjust the pacing rate of a pacemaker.

It is known that during periods of increased metabolic need, cardiac output may be optimized by adjusting various parameters in a rate-responsive pacemaker, such as heart rate, because cardiac output is the product of heart rate and stroke volume. The above-identified U.S. Pat. No. 4,708,143 describes a method where changes in stroke volume are determined from a pressure sensor and applied to a look-up table to determine a corresponding change in cardiac rate to achieve a predetermined level of cardiac output. The new cardiac rate replaces the previous rate. In this manner, the physician may set the pacemaker to an initial heart rate and the pacemaker may attempt to optimize, or at least improve, cardiac performance by adjusting the heart rate in response to changes in stroke volume, in accordance with a predetermined relationship (i.e., the look-up table).

Another patent describing stroke volume controlled rate-responsive pacing is U.S. Pat. No. 4,535,774 of Olson. Olson describes a rate-responsive pacemaker which paces the heart at a rate dependent on detected variations in the stroke volume of the heart. Olson infers stroke volume by placing an electrode system into the heart and injecting a current between these electrodes and measuring the voltage between the electrodes. Changes in the measured voltage are related to the changes in impedance of the heart cavity, with impedance changes being related to stroke volume. The inferred stroke volume is compared to a reference stroke volume, with the difference being used to compute a corresponding change in heart rate. Once again, the physician sets an initial heart rate and the pacemaker adjusts the rate to attempt to provide rate-responsive pacing therapy. Olson suggests that accuracy may be increased by using multiple electrode pairs, but that would severely increase the cost of equipment and complexity of surgery required. An additional disadvantage of Olson is that it is difficult to sense the impedance of the heart cavity during the period immediately following the delivery of pacing pulses.

Each of the aforementioned hemodynamic indicators may have certain drawbacks associated with it. One drawback is that some hemodynamic indicators, such as QT time interval, may not respond rapidly enough to optimally control cardiac pacing. Another drawback is that the measurement of these indicators may require the use of sensors that must be delivered to locations that normally do not receive electrical stimulation. Therefore, additional leads may be required which undesirably add cost to the system and complexity to the surgical procedure during which the leads are implanted. It would be desirable if the pacemaker could use physiological parameters representative of the performance of the heart during each cardiac contraction to determine a heart rate that meets the patient's current level of metabolic need.

A known rate-responsive pacemaker which also optimizes cardiac performance at rest is described in U.S. Pat. No. 5,024,222 of Thacker, which is hereby incorporated by reference in its entirety. Thacker describes a rate-responsive pacemaker which senses the physiological needs of the patient's heart using an oxygen saturation ($SO_2$) sensor and controls the pacing rate accordingly. When the patient is at rest, Thacker adjusts the pacing rate to a sub-optimal level and then adjusts the AV interval until hemodynamic performance is optimized to provide the lowest possible stimulation rate while retaining optimum cardiac performance.

Although many of the above-described hemodynamic indicators have been used in adjusting the operating parameters of the pacemaker, the physician typically sets the pacing parameters "open-loop" without knowing if the settings are hemodynamically optimal (a process where the patient returns to the physician's office periodically after the implantation for fine-tuning of the parameters). For example, while the base heart rate and AV interval are typically programmable by the physician in typical dual-chamber pacemakers, such implantable cardiac stimulating devices do not have the capability to "fine tune" these settings in a closed-loop fashion to achieve optimal cardiac performance. In fact, if the physician attempts to fine-tune the device to optimize hemodynamics, it must be performed open-loop.

In view of the deficiencies associated with the use of the IEGM or certain hemodynamic indicators, it would be desirable to provide an improved system which automatically determines the hemodynamically optimal pacemaker settings for a given patient. Ideally, such a system would use a signal that rapidly responds to sensed changes in the patient's condition (e.g., from rest to exercise), and is not subject to electrical interference from external sources or from pacemaker-induced after-potentials. During periods of activity, the system would provide an optimal heart rate. During rest, the system would provide hemodynamically optimal pacing by adjusting the base heart rate and the AV delay accordingly. Additionally, the system would provide optimal chronotropic stimulation (i.e., optimal timing of the delivered pacing pulses) to the patient by determining hemodynamically optimal pacing parameters and adjusting the device accordingly.

SUMMARY OF THE INVENTION

The disadvantages and limitations of previously known approaches for optimizing pacing therapy are overcome by the present invention. This invention is directed toward a pacemaker that includes a processing system that receives signals indicative of cardiac mechanical activity from a cardiac wall motion sensor and uses the sensor signals to derive physiologic parameters which enable the pacemaker to provide hemodynamically optimal pacing therapy. The pacing therapy may be optimized for resting periods, or for periods of metabolic need. The processing system receives signals from a cardiac wall motion sensor that is responsive to cardiac wall accelerations, and processes the raw sensor signals to derive signals representative of cardiac wall velocity and cardiac wall displacement.

Sensors that are particularly suited for use as a cardiac wall motion sensor are described in the commonly-assigned, copending U.S. patent application Ser. No. 08/091,636, filed Jul. 14, 1993, entitled "Implantable Leads Incorporating Cardiac Wall Motion Sensors and Method of Fabrication and a System and Method for Detecting Cardiac Arrhythmias Using a Cardiac Wall Motion Sensor Signal," which is hereby incorporated by reference in its entirety. That patent application discloses several types of implantable leads, including endocardial leads, myocardial active-fixation leads and epicardial patch electrodes, all of which may incorporate accelerometer-based cardiac wall motion sensors. These leads are not only useful for mechanically coupling a cardiac wall motion sensor to the cardiac wall—they may also provide the electrodes which are used to sense and administer therapeutic electrical stimulation to cardiac tissue, thereby reducing the number of leads that need to be implanted in the patient's body.

Signals provided by the above-described U.S. patent application Ser. No. 08/091,636 may be used in connection with the treatment of various cardiac arrhythmias, as described in copending, commonly-assigned U.S. patent application Ser. No. 08/154,800, filed Nov. 16, 1993, entitled "System and Method for Deriving Hemodynamic Signals from a Cardiac Wall Motion Sensor," now U.S. Pat. No. 5,430,412 which is hereby incorporated by reference in its entirety. That patent application describes a system and method of deriving cardiac wall velocity and displacement signals from cardiac acceleration signals and using the derived signals to detect and discriminate cardiac arrhythmias.

In order to overcome the disadvantages and limitations of previously known approaches for optimizing pacing therapy, the processing system of the present invention processes the derived cardiac wall motion signals (i.e., cardiac wall velocity and displacement) to produce signals representative of stroke volume, cardiac contractility, pre-ejection period and ejection time. These signals are used to provide hemodynamically optimal pacing therapy while the patient is at rest and to provide hemodynamically optimal rate-responsive pacing therapy. Stroke volume, cardiac contractility, pre-ejection period and ejection time may be used, individually or together in combination, to adjust the parameters of the implantable cardiac stimulating device so that hemodynamically optimal pacing therapy may be provided.

The signals representative of cardiac wall displacement as provided by the processing system of the present invention have been found to be related to stroke volume (i.e., the change in cardiac volume between minimum cardiac volume and maximum cardiac volume during a single heartbeat). To illustrate, a cardiac wall displacement signal from a patient suffering from cardiomyopathy (a condition where the muscle fibers of the heart experience undesired growth resulting in hemodynamically compromised cardiac performance) exhibits excursions that appear at a similar rate as normal sinus rhythm, but the amplitude of each excursion is lower than normal levels. This would indicate that the total volume of blood being pumped by the heart during each heartbeat is abnormal (perhaps pathological).

In a preferred embodiment, the processing system of the present invention utilizes cardiac wall velocity signals to assess cardiac contractility (a measure of cardiac performance based on the maximum change in cardiac fiber length per unit time for a given cardiac excitation). Normally, during exercise and periods of stress (both physiologic and psychological) contractility increases to provide the ability to increase cardiac power and thus increase the work capability of the heart.

Cardiac performance may be measured by multiplying the maximum cardiac wall velocity signal by the force required to empty the heart chamber (the result is a measure of the power that the cardiac muscle is capable of providing). The derived cardiac wall velocity signals may be processed to determine the maximum rate of change in ventricular volume (the initial slope in the aortic blood flow). This is directly proportional to contractility, and thus may be used in relation to known contractility indices (see, for example, Berne, R. M. and Levy, M. N., *Cardiovascular Physiology*, C. V. Mosbey Company: St. Louis, pp. 78–82 (1981)). The processing system of the present invention may use the determined contractility to establish heart rate during periods of metabolic need or other periods of stress by setting the heart rate in accordance with the patient's correlation to the contractility indices.

Another parameter that may be easily assessed by the present invention using the cardiac wall motion sensor signals is pre-ejection period (the time between stimulus—R-wave—and the beginning of mechanical contraction of the heart). The pre-ejection period, which may be determined based on cardiac wall velocity or acceleration signals and electrocardiogram, is related to the degree of cardiac sympathetic stimulation. Thus, it may also be used by the system of the present invention to adjust heart rate to provide hemodynamically optimal pacing therapy.

An alternative embodiment of the present invention uses cardiac wall motion sensor signals to determine the ejection time (the time between the onset of a cardiac contraction and the end of the contraction, or the time required for a "full" heart cavity, such as the left or right ventricle, to empty) by measuring the onset and termination of a cardiac contraction. Because changes in the ejection time are directly related to stroke volume, cardiac pacing therapy may also be optimized by adjusting the AV interval, thereby adjusting the ejection time.

The present invention is directed to a processing system which processes the cardiac wall displacement signals to determine cardiac stroke volume, and then uses the calculated stroke volume to optimize the timing of the stimulation provided to the patient by the rate-responsive pacemaker. In this manner, operational parameters of the rate-responsive pacemaker may be adjusted, in a closed loop manner, as the circumstances for optimal hemodynamic performance change. For example, the rate-responsive pacemaker of the present invention may continually adjust the heart rate of the patient to provide hemodynamically optimal pacing therapy, thereby substantially maximizing cardiac output, which is especially advantageous for patients suffering from chronotropic incompetence (when the electrical stimulation at the sinus node is too slow). Alternatively, the present invention may utilize cardiac wall velocity to derive cardiac contractility, pre-ejection period, or ejection time. Each of these parameters may also be used to enable the rate-responsive pacemaker to provide hemodynamically optimal pacing therapy during periods of metabolic need.

Additionally, for certain patients, especially those suffering from heart failure conditions where the ability of the myocardium to perform work is diminished, the present invention provides hemodynamically optimal pacing therapy at rest. Normally, as preload increases (the pressure that fills the ventricles, commonly known as the end-diastolic pressure), cardiac output increases, but the ability of the heart to work has been diminished and preload remains elevated. To maintain blood pressure, the afterload also increases, thereby requiring the heart to work even harder.

Current techniques to relieve the patient typically include the use of drugs (e.g., norepinephrine or digitalis) to increase contractility and reduce blood pressure. By increasing cardiac performance at rest using hemodynamically optimal pacing therapy based on cardiac wall motion sensor signals, the present invention reduces the need to treat cardiac failures with drugs. The present invention initially establishes optimal values for heart rate and AV interval. Then, for each optimization cycle, cardiac performance is measured using cardiac wall motion sensor signals for selected combinations of heart rate and AV interval. The heart rate/AV interval values resulting in the greatest measured cardiac performance become the new optimal values for the next cycle.

In another aspect of the present invention, methods for providing hemodynamically optimal rate-responsive pacing therapy and hemodynamically optimal pacing therapy at rest are described. The methods of providing hemodynamically optimal pacing therapy (for rate-response or at rest) may utilize, individually or in combination, stroke volume (as derived from cardiac displacement), contractility (as derived from cardiac velocity), pre-ejection period (as derived from cardiac velocity) and ejection time (which is related to stroke volume), to optimize cardiac output.

The present invention also provides a pacemaker that uses a signal provided by a cardiac wall motion sensor delivered to cardiac tissue by an implantable lead, to determine the parameters necessary to provide hemodynamically optimal rate-responsive pacing therapy and to provide hemodynamically optimal pacing therapy during rest. The implantable system adjusts those parameters (such as heart rate and AV interval) to provide the patient with optimal cardiac output.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Figure 1:
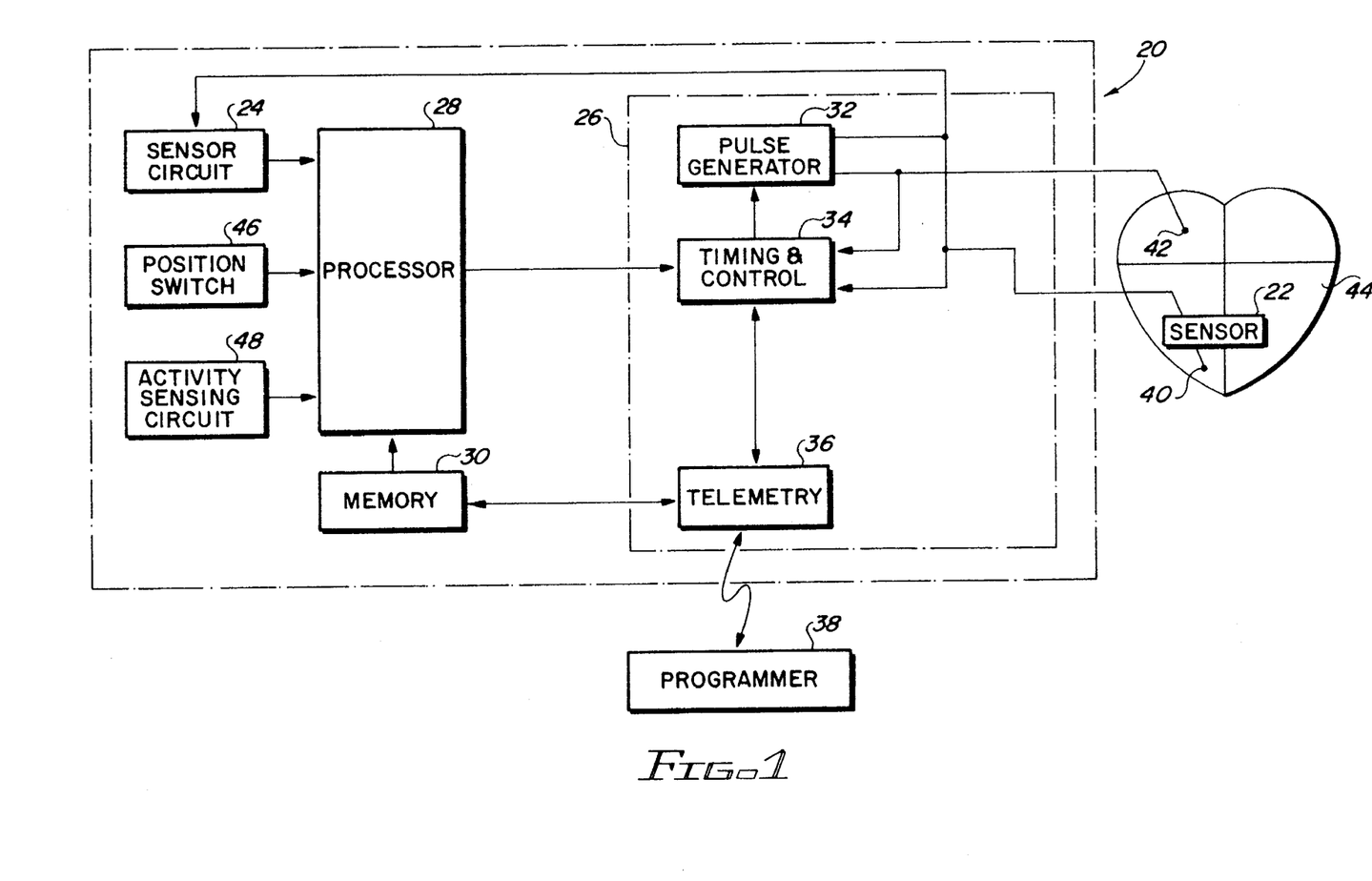
FIG. 1 is a block diagram of a preferred embodiment of a dual chamber implantable pacemaker which uses cardiac wall motion sensor signals to administer hemodynamically optimal therapeutic electrical stimulation to cardiac tissue in accordance with the principles of the present invention.

FIG. 1 shows a dual chamber implantable pacemaker 20 which operates to provide pacing pulses at a rate that comfortably meets the patient's metabolic demands, while also providing hemodynamically optimal pacing therapy at rest. The pacemaker 20 preferably uses signals generated by a cardiac wall motion sensor 22 to determine the extent to which the patient is engaged in physical activity—the measured level of activity being indicative of metabolic need. Alternatively, the pacemaker 20 may use a dedicated activity sensor (not shown) to determine metabolic demands. Preferably, the sensor 22 is a cardiac wall motion sensor, as described in the above-incorporated U.S. patent application Ser. No. 08/091,636.

The signals generated by the sensor 22 are initially received by a sensor circuit 24. Several designs for the sensor circuit 24 have been used in previously known implantable medical devices, and one such design is described in greater detail below in connection with FIGS. 2 and 3.

In addition to the sensor 22 and the sensor circuit 24, the pacemaker includes a pacemaker circuit 26 (which may be conventional), a processor 28 coupled to the sensor 22, and a memory circuit 30 coupled to the processor 28. The pacemaker circuit 26 includes a pulse generator circuit 32, a timing and control circuit 34 coupled to the pulse generator circuit 32 and to the processor 28, and a telemetry circuit 36. The telemetry circuit 36, which telemetrically communicates with an external programmer 38, is coupled within the pacemaker to the memory circuit 30 and the timing and control circuit 34.

Coupled to the pulse generator circuit 32 are at least two conventional pacing leads 40 and 42 (although more pacing leads can be used if needed). The pacing leads 40 and 42 are used to deliver pacing pulses provided by the pulse generator circuit 32 to the patient's heart 44. In addition, the pacing leads 40 and 42 sense the natural rhythm of the heart 44 (e.g., the patient's IEGM), and present signals indicative thereof to the timing and control circuit 34. More precisely, the lead 42 senses atrial activity, and the lead 40 senses ventricular activity. The ability to sense the natural rhythm of the heart 44 enables the pacemaker to operate in a demand mode, in which delivery of a pacing pulse is inhibited by the timing and control circuit 34 when a naturally occurring cardiac contraction is sensed during the escape interval following a preceding contraction.

The pacemaker 20 may also include a position switch 46 to monitor whether the patient is supine. The switch 46 may be, for example, a mercury switch or any other conventional switch which senses the patient's orientation (horizontal versus vertical). Additionally, an activity sensing circuit 48 (including a dedicated activity sensor) may be provided within the pacemaker 20 to monitor the activity level of the patient.

Although the following description assumes that the pacemaker operates in a demand mode, it should be understood that a simpler implementation is possible, in which the pacemaker does not inhibit delivery of pacing pulses when naturally occurring contractions are sensed. Also, demand mode may be a telemetrically programmable feature, allowing the pacemaker to be switched into and out of demand mode when desired by a physician.

In operation, the sensor 22 generates electrical potentials corresponding to cardiac wall acceleration when the sensor 22 experiences cardiac wall motion. The signals generated by the sensor 22 are initially processed by the sensor circuit 24 (described below), after which they are received by the processor 28.

The processor 28 may further process the sensor signals using conventional techniques (e.g., averaging, half-wave rectification, full-wave rectification) in order to derive a measurement of the patient's current level of physical activity. The processor 28 then uses the processed sensor signals to generate a rate control signal which is provided to the timing and control circuit 34. The timing and control circuit 34 uses the rate control signal to adjust the heart rate maintained by the pacemaker. In a preferred embodiment, the rate control signal provided by the processor 28 adjusts the heart rate used by the timing and control circuit 34, which has the effect of increasing or decreasing the maintained heart rate.

The manner by which the pacemaker 20 delivers pacing therapy is controlled by the processor 28, to some extent, in accordance with parameters stored in the memory 30. Many of these parameters are known in the art (i.e., escape interval, refractory period, etc.), and they may be programmed by a medical practitioner using the programmer 38 that communicates with the processor 28 through the telemetry circuit 36.

However, static parameters stored in the memory 30 do not provide the processor 28 with all of the information necessary to control the manner by which therapies are administered by the pacemaker 20. Rather, it is necessary for the processor 28 to receive information pertaining to the patient's current cardiac condition in order to optimize cardiac hemodynamic performance, during periods of metabolic need and at rest, so that the patient receives optimal chronotropic stimulation from the implantable cardiac stimulating device.

In a preferred embodiment of the present invention, the processor 28 receives information from the sensor circuit 24 in the form of cardiac wall displacement signals, cardiac wall velocity signals, and raw cardiac acceleration signals. The cardiac wall displacement signals and the cardiac wall velocity signals are derived from the raw acceleration signals provided by a cardiac wall motion sensor 22. These signals are not subject to interference from after-potentials, and unlike certain other hemodynamic indicators, they allow the processor 28 to rapidly respond to changing metabolic conditions and to maintain hemodynamically optimal chronotropic stimulation for the patient at rest.

Although the processor 28 may be programmed by a medical practitioner via the telemetry circuit 36 to operate in one of several modes, one of the advantages of the present invention is that the processor 28 can fine tune the parameters set by the practitioner to achieve hemodynamically optimal performance. For example, the processor 28 may be initially programmed to establish a given AV interval in the patient. The processor 28 may then adjust the AV interval based on the determination of current stroke volume (as determined from the cardiac wall displacement signals), contractility, pre-ejection period, or ejection time (as determined from the cardiac wall velocity signals and raw acceleration signals).

Figure 2:
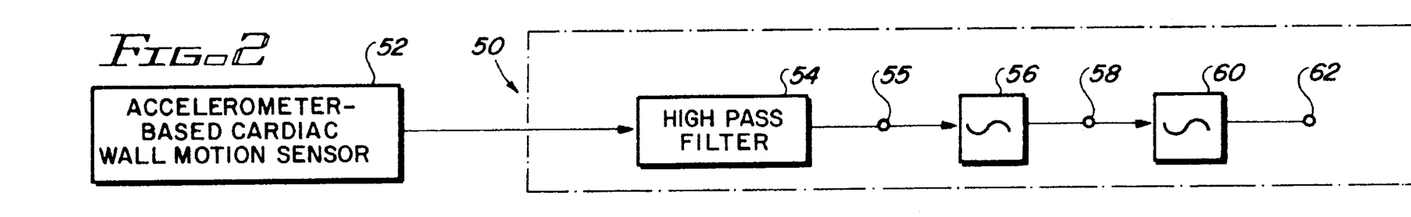
FIG. 2 is a block diagram of a preferred embodiment of a processing system for deriving cardiac wall displacement and cardiac wall velocity.

Referring to FIG. 2, a processing system 50 for deriving an improved hemodynamic indicator is described (the processing system 50 may function as the sensor circuit 24 in FIG. 1). This system is disclosed in the above-incorporated U.S. patent application Ser. No. 08/154,800. That patent application describes a system and method for deriving cardiac wall velocity and displacement signals from cardiac wall acceleration signals and using the derived signals to detect and discriminate cardiac arrhythmias.

The processing system 50 is intended to receive input signals from an accelerometer-based cardiac wall motion sensor 52 (which may be substantially similar to sensor 22 of FIG. 1). The cardiac wall motion sensor 52 is mechanically coupled to a region of a patient's cardiac wall (not shown) in a manner that allows the cardiac wall motion sensor 52 to respond to cardiac wall accelerations associated with cardiac contractile activity. Sensors that are particularly suited for use as the cardiac wall motion sensor 52 are described in the above-incorporated U.S. patent application Ser. No. 08/091,636, filed Jul. 14, 1993. As previously described, that patent application discloses several types of implantable leads, including endocardial leads, myocardial active-fixation leads and epicardial patch electrodes, all of which may incorporate accelerometer-based cardiac wall motion sensors.

The processing system 50 includes a high pass filter 54, which receives raw acceleration signals from the cardiac wall motion sensor 52. The high pass filter 54 selects signals associated with cardiac wall motion, and rejects unwanted signals, such as those associated with body motion (in a manner described in greater detail below). The filtered acceleration signals 55 are received by a first integrator circuit 56, which integrates the filtered acceleration signals over time to derive cardiac wall velocity signals which are made available at a node 58.

The velocity signals derived using the first integrator circuit 56 are received by a second integrator circuit 60, which integrates the velocity signals over time to derive cardiac wall displacement signals, which are made available at a node 62. The displacement signals are made available at an output terminal 62 for use in connection with providing hemodynamically optimal pacing therapy.

The precise manner by which the processing system 50 is implemented may be varied without departing from the spirit of the invention. For example, the processing system 50 may be implemented using discrete analog components (see FIG. 3 below) or digital components, or some combination of the two. Preferably, the processing system 50 is implemented using integrated circuitry on a hybrid (not shown) of an implantable cardiac stimulating device (described above in connection with FIG. 1). In an alternative embodiment of the invention, some or all of the processing steps described above may be accomplished by a processor (shown in FIG. 1) in the implantable cardiac stimulating device. For a processor-based embodiment, the block diagram of FIG. 2 represents a sequence of processing steps which may be performed by the processor.

Figure 3:
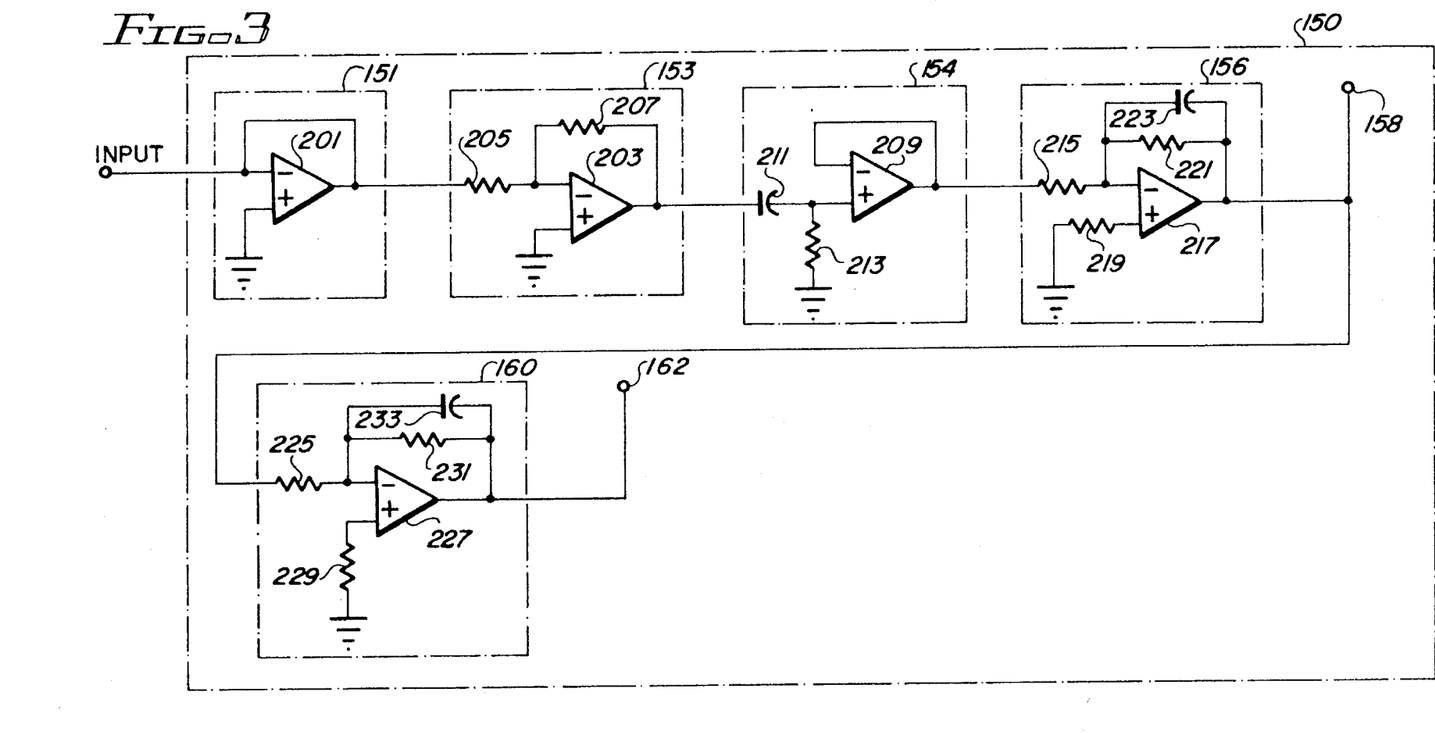
FIG. 3 is a schematic diagram of a preferred embodiment of the processing system of FIG. 2 which is implemented using analog circuitry.

A preferred embodiment of the processing system 50 (FIG. 2) which is implemented using analog circuitry that may be conveniently integrated into hybridized circuitry of an implantable cardiac stimulating device is shown in FIG. 3. For ease in comparing the components shown in FIG. 3 to the block diagram of FIG. 2, like components are numbered using essentially the same reference numerals, except that they are prefixed by "1" in FIG. 3.

A processing system 150 preferably includes a buffer 151 which receives the raw acceleration signals from the cardiac wall motion sensor 52 (FIG. 2). The buffer 151 is used for impedance matching to downstream circuitry without introducing any phase shift. The buffer 151 may be implemented using a conventional operational amplifier 201 which has its inverting input coupled to its output.

The buffer 151 may be coupled to an amplifier 153 to increase the strength of the input signals. The amplifier 153 may comprise an operational amplifier 203, a first bias resistor 205 (coupled between the output of the operational amplifier 201 and the inverting input of the operational amplifier 203) and a second bias resistor 207 (coupled between the inverting input and the output of the operational amplifier 203). The bias resistors 205 and 207 (which may both have resistances of about 25 K$\Omega$) are used to set the gain of the amplifier 153. As is known in the art, the gain of the amplifier 153 may be changed by altering the ratio of the second bias resistor 207 to the first bias resistor 205. For example, changing the value of the first bias resistor to about 5 K$\Omega$ would change the gain (i.e., the ratio of the resistor 207 to the resistor 205) from about 1 to about 5. The precise gain is dependent on the sensor output level and may be best adjusted at manufacture.

The amplifier 153 is preferably coupled to a high pass filter 154 which includes an operational amplifier 209, a capacitor 211 (coupled between the output of the operational amplifier 203 and the non-inverting input of the operational amplifier 209) and a resistor 213 (coupled between the non-inverting input of the operational amplifier 209 and ground) having a resistance of about 14 KΩ. Varying the capacitance of the capacitor 211 will correspondingly vary the frequency threshold of the high pass filter 154. To reduce signals corresponding to body motion and respiration (which typically fall within the range of about 0.1 Hz to less than 6 Hz) the capacitance of the capacitor 211 may be varied between about 47 µF and about 0.092 µF.

The high pass filter 154 produces the high pass filtered accelerometer output 155 that is made available to the processor 28. The high pass filter 154 is preferably coupled to a first integrator circuit 156 which includes an operational amplifier 217, a first resistor 215 (coupled between the output of the high pass filter 154 and the inverting input of the operational amplifier 217), a second resistor 219 (coupled between the non-inverting input of the operational amplifier 217 and ground), a third resistor 221 (coupled between the output and the inverting input of the operational amplifier 217), and a capacitor 223 connected in parallel with the resistor 221. The resistor 215 has a resistance of about 2.5 KΩ, while the resistors 219 and 221 may have resistances of about 2.2 KΩ and 25 KΩ respectively. The capacitor 223 has a capacitance of about 4.7 µF. The output of the first integrator circuit 156 may be connected to an output terminal 158, in order to provide signals representative of cardiac wall velocity.

The second integrator circuit 160 (which is essentially identical to the first integrator circuit 156) preferably includes an operational amplifier 227, three resistors 225, 229 and 231, and a capacitor 233. The resistors 225, 229 and 231, and the capacitor 233 have about the same values as, respectively, the resistors 215, 219 and 221, and the capacitor 223. The output of the second integrator circuit 160 may be coupled to an output terminal 162 to provide cardiac wall displacement signals.

Regardless of the specific nature by which the cardiac wall motion sensor data (acceleration and velocity) are processed, the present invention utilizes this data to provide hemodynamically optimal rate-responsive pacing therapy and hemodynamically optimal pacing therapy at rest. The processing system of the present invention provides a highly accurate and reliable determination of at least the following cardiac performance parameters: stroke volume, contractility, pre-ejection period and ejection time through the use of a cardiac wall motion sensor. These parameters may be measured, as described below in connection with FIG. 4, from the cardiac wall motion sensor signals which may be processed to derive cardiac wall acceleration, velocity and displacement signals.

Figure 4:
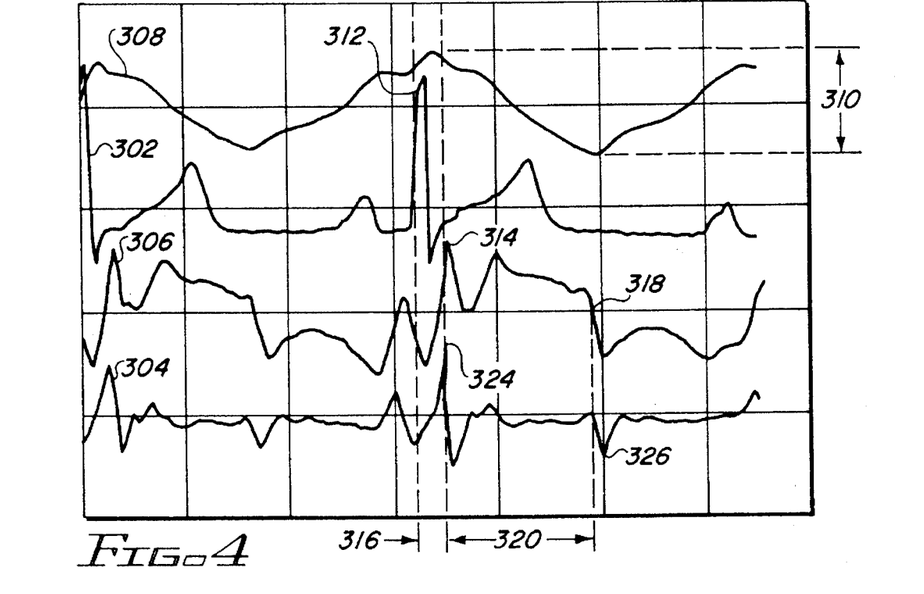
FIG. 4 is a graph showing a displacement signal, an electrocardiogram (ECG), a velocity signal and an acceleration signal, all plotted as a function of time.

FIG. 4 shows an electrocardiogram 302, a cardiac acceleration signal 304, a cardiac velocity signal 306 and a cardiac displacement signal 308, all plotted versus time. The acceleration signal 304 was derived from a cardiac wall motion sensor, as described above in connection with FIGS. 1–3. The velocity signal 306 and the displacement signal 308 were derived from the acceleration signal 304 as described above in connection with FIGS. 2 and 3.

Although stroke volume is a known parameter that may be used as a control signal in rate-responsive pacemakers, known techniques for providing stroke volume may have deficiencies, as described above. The present invention overcomes these deficiencies by deriving stroke volume signals from cardiac wall motion sensor signals. In deriving stroke volume from cardiac wall motion signals, the ventricle may be modeled as a sphere, and thus, the cardiac displacement can be regarded as the change in the radius of the heart. As long as radius changes are relatively small, the radius is approximately proportional to ventricular volume, as shown by the following equation which represents the Taylor series expansion of volume with respect to radius:

$$v = V(X_0) + (\Delta X(t)/1!)*(dV(X_0)/dr) + (\Delta X^2(t)/2!)*(d^2V(X_0)/dr^2) + \quad (1)$$

Therefore, the Taylor series expansion relates the linear dimension (cardiac wall displacement) to a cubic dimension (stroke volume). Small changes in the excursion between the minimum and maximum of displacement result in corresponding changes in stroke volume (because the Taylor series may be truncated after the first two terms). Thus, stroke volume may be determined by calculating the difference between the minimum and maximum displacement, as shown by difference 310, based on cardiac wall motion sensor signals, for an individual heartbeat. In this manner, the second integral of the cardiac acceleration signals (i.e., cardiac wall displacement, as described above in connection with FIGS. 2 and 3) is used to provide stroke volume in a highly accurate and reliable manner so that an implantable cardiac stimulating device may rely on the stroke volume data during all phases of the delivery of pacing pulses.

Another known parameter for controlling a rate-responsive pacemaker is contractility, which may also be advantageously derived, in accordance with the principles of the present invention, from cardiac wall motion sensor signals. Because contractility is a measure of cardiac performance based on the maximum change in cardiac fiber length per unit time for a given cardiac excitation, contractility may be derived from cardiac wall velocity signals (i.e., the change in cardiac fiber length is proportional to the change in cardiac wall velocity). Measurements of contractility may be made by sampling the cardiac wall velocity signals for a given time period, preferably 250 milliseconds, following each R-wave 312 or stimulation pulse. The samples are then analyzed to determine the maximum cardiac wall velocity 314 during the sampling period, which is proportional to the contractility during the measured heartbeat.

Pre-ejection period is also a known parameter which may be used in controlling rate-responsive pacemakers. As with the previously described parameters (i.e., stroke volume and contractility), pre-ejection period may also be advantageously determined from cardiac wall motion sensor signals. Pre-ejection period is typically defined as the time from the occurrence of the R-wave 312 to the onset of a cardiac contraction. The onset of a cardiac contraction correlates to the maximum cardiac wall velocity 314. Therefore, measurements of pre-ejection period may be made by sampling the cardiac wall velocity signal for a given time period after the R-wave 312 (or stimulation), preferably 25 milliseconds. The measured pre-ejection period, as indicated by a difference 316, is determined by measuring the time between the R-wave 312 and the occurrence of the maximum cardiac wall velocity signal 314. In view of the fact that pre-ejection period naturally varies as a person undergoes activity, measured changes in pre-ejection period provide a reliable parameter with which to control pacing in rate-responsive pacemakers.

Ejection time, another known parameter which may be used to control a rate-responsive pacemaker, may also be advantageously determined from derived cardiac wall motion signals. Under natural conditions (i.e., no artificial pacing), ejection time is typically defined as the time between the onset of a cardiac contraction and the end of the contraction. Measurements of ejection time may be made by first sampling the cardiac wall velocity signal for a given time period, preferably 250 milliseconds. As described above in connection with the discussion of pre-ejection period, the onset of a contraction coincides to the maximum cardiac wall velocity 314, while the termination of a cardiac contraction correlates to the point where the cardiac wall velocity crosses zero 318. The time between these two measured events is the ejection time, as indicated by the period 320. Alternatively, the high pass filtered accelerometer signal 155 from FIG. 3, may be used to compute ejection time. Referring to FIG. 4, the accelerometer waveform 304 displays a positive peak 324 that nearly coincides in time with the velocity peak 314. The acceleration waveform 304 displays a negative peak 326 that nearly coincides with the velocity zero-crossing at 318. Measuring the time difference between the occurrence of the positive peak 324 and the negative peak 326 provides an estimate of ejection time very similar in value to the period 320. Consequently, the velocity 306 or the acceleration 304 may be used to compute ejection time. Also, because the ejection time naturally increases as an individual engages in exercise, measurement of changes in ejection time may be used as a reliable indication of a need to increase heart rate in a rate-responsive pacemaker.

Figure 5:
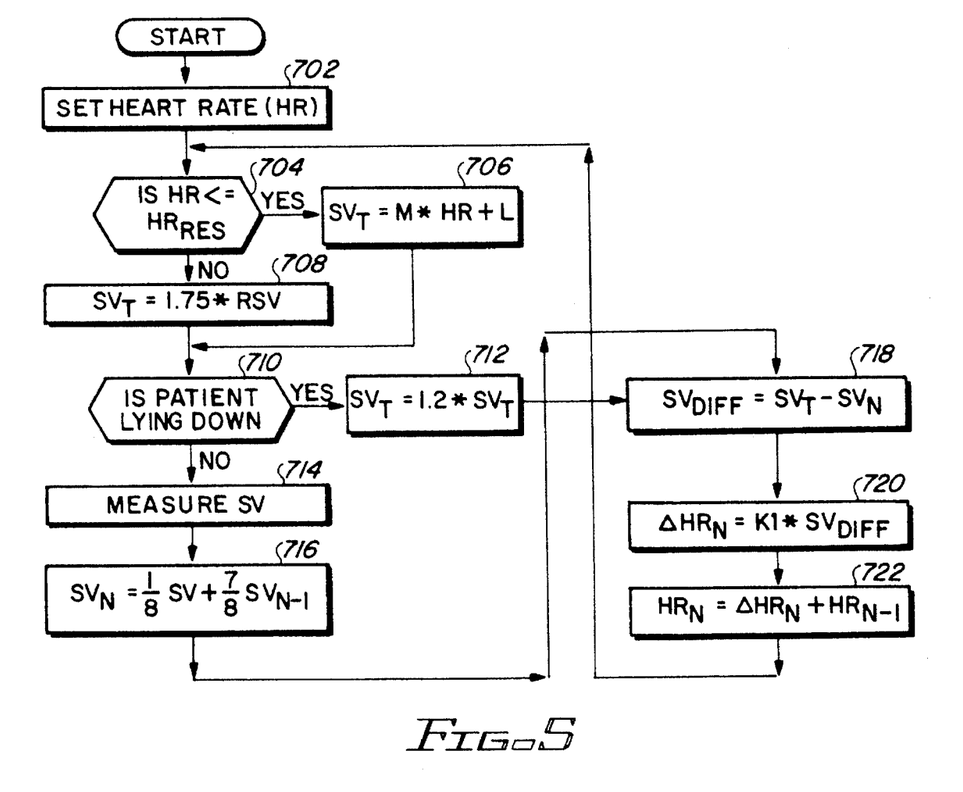
FIG. 5 is a logic flow diagram showing how the processing system of the present invention adjusts the heart rate of a patient in accordance with metabolic demands in response to changes in stroke volume as derived from signals from a cardiac wall motion sensor.

Referring now to FIGS. 5–10, a series of logic flow diagrams are described which represent a control program executed by the processor 28 of FIG. 1. In one embodiment of the present invention, the processing system of the present invention utilizes the processor 28 (FIG. 1) to analyze the derived cardiac wall motion sensor signals and to determine the corresponding stimulation pulse parameters to achieve hemodynamically optimal performance for a rate-responsive pacemaker during periods of exercise. FIG. 5 is a logic flow diagram showing how the processor 28 (FIG. 1) adjusts heart rate in response to changes in stroke volume (SV) as derived from signals from a cardiac wall motion sensor.

Referring first to FIG. 5, the control program starts when a start-up command is received from the external programmer 38 (FIG. 1) through the telemetry circuit 36 (FIG. 1). This command may be sent in connection with the implantation procedure (before, during, or after), and during subsequent follow-up visits.

After start-up, the processor 28 (FIG. 1) performs an initialization step 702, at which the pacemaker 20 (FIG. 1) acquires an initial base heart rate (BR) from the external programmer 38 (FIG. 1) through the telemetry circuit 36 (FIG. 1), the base heart rate (BR) then being stored in the memory 30 (FIG. 1). Also during the step 702, the physician sets a maximum sensor rate (MSR) to be the highest value for heart rate (HR) which is measurable by the sensor 22 (FIG. 1), such that BR and MSR define a range of valid heart rates for the control program.

As part of the step 702, the processor 28 calculates the heart rate at maximum stroke volume ($HR_{MSV}$) to a value corresponding to a maximum value for stroke volume (i.e., a value for heart rate above which stroke volume be kept constant), preferably defined as shown in Equation 2, as follows:

$$HR_{MSV}=BR+0.4*(MSR-BR) \qquad (2)$$

Also as part of the step 702, and in connection with or immediately following the implantation procedure, the physician measures the patient's resting stoke volume (RSV) with the rate programmed to base rate (BR) while the patient is upright and programs the pacemaker 20 (FIG. 1) with the measured value.

During the processing of a set of steps 704–706, the processor 28 (FIG. 1) sets a target stroke volume ($SV_T$) based on the previous value of the measured heart rate (HR) (for the initial pass through steps 704–706, the previous value of HR is set to be equal to BR). At the test 704, the processor 28 determines whether HR is less than or equal to $HR_{MSV}$. If HR is less than or equal or $HR_{MSV}$, the processor 28, at a step 706, determines $SV_T$ in accordance with Equation 3, as follows:

$$SV_T=m*HR+L \qquad (3)$$

In Equation 3, m is defined as being equal to 1.75 times RSV divided by the difference between MSR and BR, which represents the slope of a line defining part of the relationship between heart rate and stroke volume. Additionally, L is defined as being equal to RSV multiplied by the term equal to 1 minus 1.75 times BR divided by the difference between MSR and BR, which represents the y-intercept of a line defining the relationship between heart rate and stroke volume.

If HR is greater than $HR_{MSV}$, the processor 28, at a step 708, sets $SV_T$ to be equal to 1.75 times RSV, as shown by Equation 4:

$$SV_T=1.75*RSV \qquad (4)$$

The steps 704–708, therefore establish the proportional relationship between the target stroke volume and heart rate, such that the target stroke volume varies as heart rate increases from BR to $HR_{MSV}$, and at heart rates above $HR_{MSV}$, the target stroke volume remains constant.

After $SV_T$ has been set, the processor 28 (FIG. 1) determines whether the patient is lying down, preferably through the use of the position switch 46 (FIG. 1), at a test 710. If the patient is supine, the processor 28 (FIG. 1) increases $SV_T$ by setting $SV_T$ equal to the product 1.2 times RSV to achieve a corresponding decrease in HR at a step 712, as would normally occur when a person without a pacemaker lies down (without this step, the processor 28 (FIG. 1) would cause HR to increase upon lying down, due to the increase in preload in the heart).

The processor 28 (FIG. 1) measures SV based on cardiac wall displacement signals, as described above in connection with FIG. 4, at a step 714. At a step 716, the processor 28 (FIG. 1) produces a running average of estimated stroke volume ($SV_N$) based on input signals from the cardiac wall motion sensor 22 (FIG. 1), as shown in Equation 5, using a recursive low-pass filter to derive a digitally smoothed representation of SV.

$$SV_N=(1/8)*SV+(7/8)*SV_{N-1} \qquad (5)$$

The variable designated as $SV_N$ contains the digitally smoothed representation of the patient's stroke volume. At a heart rate of 60 bpm, the digital filter defined by Equation 5 has a time constant of approximately 8 seconds. The variable designated $SV_{N-1}$ represents the value of $SV_N$ derived using Equation 5 during the previous cardiac cycle ($SV_{N-1}$ is set to be equal to $SV_T$ until actual measured values for $SV_N$ exist).

At a step 718, the processor 28 (FIG. 1) computes a value for the variable designated as $SV_{DIFF}$, as illustrated by Equation 6, which is the difference between $SV_T$ and $SV_N$.

$$SV_{DIFF}=SV_T-SV_N \qquad (6)$$

At a step 720, the processor 28 (FIG. 1) multiplies this difference by a proportionality constant (K1), which is preferably −600, but may vary between −200 and −1000, to determine the required change in HR ($\Delta HR_N$). Finally, the processor 28 (FIG. 1) sums $\Delta HR_N$ with the previous value for HR ($HR_{N-1}$) at a step 722, as shown by Equation 7 and then returns to the step 704 (to determine the affect of the new value of $HR_N$ on $SV_T$).

$$HR_N = \Delta HR_N + HR_{N-1} \qquad (7)$$

Figure 6:
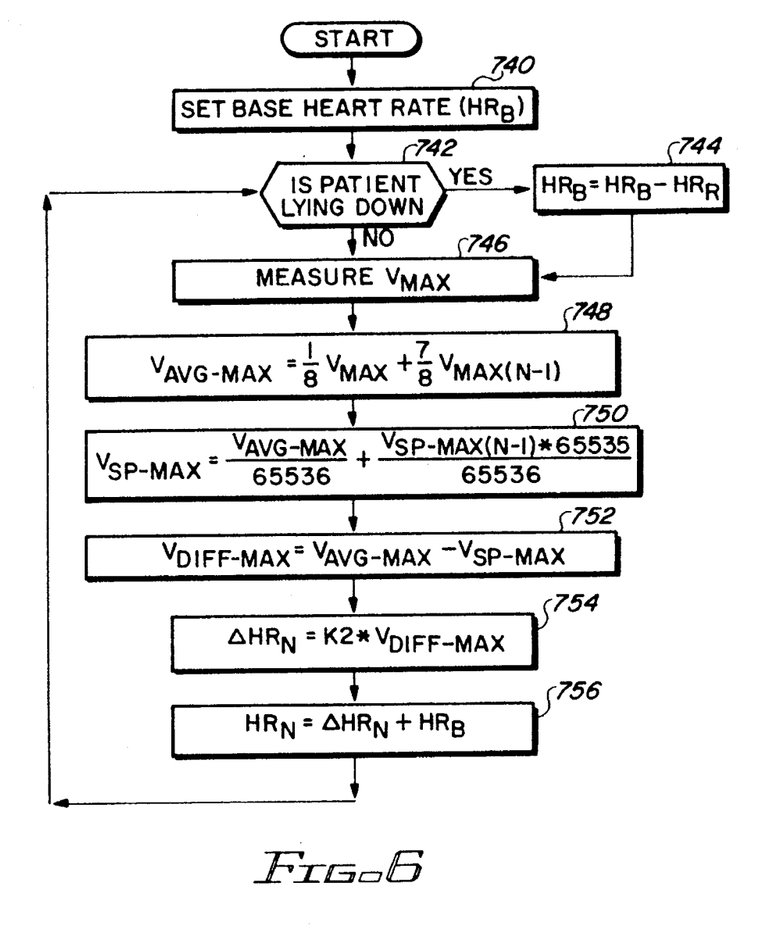
FIG. 6 is a logic flow diagram showing how the processing system of the present invention adjusts the heart rate of a patient in accordance with metabolic demands in response to changes in contractility as derived from signals from a cardiac wall motion sensor.

Referring now to FIG. 6, a flow diagram showing another embodiment of the present invention in which the processor 28 (FIG. 1) adjusts heart rate (HR) in response to changes in contractility as derived from signals from a cardiac wall motion sensor. The control program starts when a start-up command is received from the external programmer 38 (FIG. 1) through the telemetry circuit 36 (FIG. 1).

After start-up, the processor 28 (FIG. 1) performs an initialization step 740, at which the pacemaker 20 (FIG. 1) acquires an initial base rate ($HR_B$) and other operating parameters from the external programmer 38 (FIG. 1) (which is set by the physician) through the telemetry circuit 36 (FIG. 1). The base rate, as well as the other operating parameters, then being stored in the memory 30 (FIG. 1). The processor 28 conducts a test 742 of the position switch 46 (FIG. 1) to determine whether the patient is lying down. If the patient is supine, the processor 28 (FIG. 1) reduces the base heart rate by a predetermined amount ($HR_R$), preferably 10–25 bpm (as input by the physician and set in the initialization step 740), at a step 744 or set, while the patient is laying down, at a later date using the programmer 38 (FIG. 1).

At a step 746, the processor 28 (FIG. 1) computes the value of the maximum cardiac wall velocity ($V_{MAX}$) for the current heartbeat, which, as described above in connection with FIG. 4, is proportional to the physiologic parameter contractility. At a step 748, the processor 28 (FIG. 1) produces a running average of estimated maximum cardiac wall velocity ($V_{AVG-MAX}$) based on input signals from the cardiac wall motion sensor 22 (FIG. 1), as shown in Equation 8, using a recursive low-pass filter to derive a digitally smoothed representation of $V_{MAX}$.

$$V_{AVG-MAX} = (1/8) * V_{MAX} + (7/8) * V_{AVG-MAX(N-1)} \qquad (8)$$

The variable designated as $V_{AVG-MAX}$ contains the digitally smoothed representation of the patient's maximum cardiac wall velocity. At a heart rate of 60 bpm, the digital filter defined by Equation 8 has a time constant of approximately 8 seconds. The variable designated $V_{AVG-MAX(N-1)}$ represents the value of $V_{AVG-MAX}$ derived using Equation 8 during the previous cardiac cycle ($V_{AVG-MAX(N-1)}$ is initially input by the physician at an estimated optimal value for the patient and set by the processor 28 during the initialization step 740). The processor 28 (FIG. 1) uses the computed value of $V_{AVG-MAX}$ to produce an eighteen-hour running average of $V_{MAX}$ ($V_{SP-MAX}$) at a step 750, as shown in Equation 9.

$$V_{SP-MAX} = V_{AVG-MAX}/65536 + (V_{SP-MAX(N-1)} * 65535)/65536 \qquad (9)$$

The variable designated as $V_{SP-MAX}$ contains the further digitally smoothed representation of the patient's maximum cardiac wall velocity. At a pacing rate of 60 bpm, the time constant of this digital filter is approximately 18 hours. The variable designated $V_{SP-MAX(N-1)}$ represents the value of $V_{SP-MAX}$ derived using Equation 9 during the previous cardiac cycle.

The processor 28 (FIG. 1) determines the difference between the two filtered representations of maximum cardiac velocity (the 8 second representation and the 18 hour representation) at a step 752, as shown by Equation 10.

$$V_{DIFF-MAX} = V_{AVG-MAX} - V_{SP-MAX} \qquad (10)$$

The processor 28 (FIG. 1) multiplies the computed value of $V_{DIFF-MAX}$ by a proportionality constant (K2), which is preferably 100 bpm/cm/sec, but may vary between 600 bpm/cm/sec and 30 bpm/cm/sec, to determine the required change in the heart rate ($\Delta HR_N$) at a step 754. K2 has a large range because it is somewhat dependent on location within the heart and specifically how the primary acceleration vector aligns with the most sensitive orientation of the accelerometer. Finally, the processor 28 (FIG. 1) sums $\Delta HR_N$ with $HR_B$ at a step 756, as shown by Equation 11, and then returns to the step 742.

$$HR_N = \Delta HR_N + HR_B \qquad (11)$$

Figure 7:
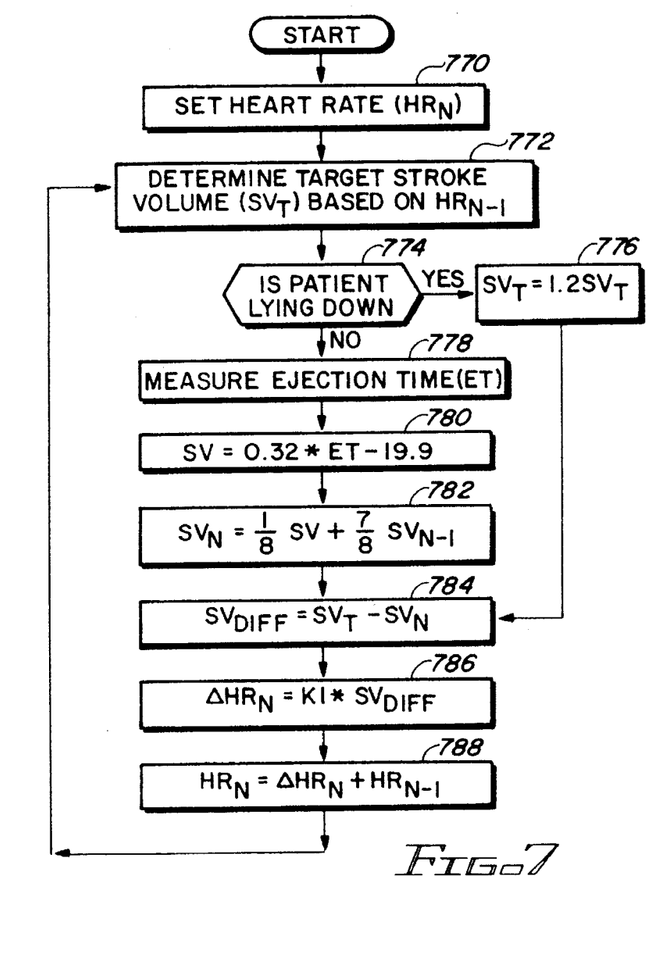
FIG. 7 is a logic flow diagram showing how the processing system of the present invention adjusts the heart rate of a patient in accordance with metabolic demands in response to changes in ejection time as derived from signals from a cardiac wall motion sensor.

An embodiment of the present invention which provides hemodynamically optimal rate-responsive pacing during periods of metabolic need based on a determination of ejection time is shown in FIG. 7. As described above in connection with FIG. 4, ejection time is directly proportional to stroke volume, and thus may also be used as a reliable optimization parameter. Referring now to FIG. 7, the control program starts when a start-up command is received from the external programmer 38 (FIG. 1) through the telemetry circuit 36 (FIG. 1).

After start-up, the processor 28 (FIG. 1) performs an initialization step 770, at which the pacemaker 20 (FIG. 1) acquires an initial heart rate ($HR_N$) and other operating parameters from the external programmer 38 (FIG. 1) through the telemetry circuit 36 (FIG. 1), the base rate and other operational parameters then being stored in the memory 30 (FIG. 1). At a step 772, the processor 28 (FIG. 1) sets the target stroke volume ($S_{VT}$) based on the previous value of the heart rate ($HR_{N-1}$), as described in connection with steps 704–708 above.

The processor 28 (FIG. 1) determines whether the patient is lying down, preferably through the use of the position switch 46 (FIG. 1) at a test 774. If the patient is supine, the processor 28 (FIG. 1) increases $SV_T$ by setting $SV_T$ equal to 1.2 times RSV to achieve a corresponding decrease in HR at a step 776, as would normally occur when a person without a pacemaker lies down (as described above, without this step, the processor 28 (FIG. 1) would cause HR to increase upon lying down, due to the increase in preload in the heart).

The processor 28 (FIG. 1) measures ejection time (ET), as described above in connection with FIG. 4, at a step 778. The processor 28 calculates a value for stroke volume (SV) from the measured value of ET at a step 780, as shown by Equation 12 (this relationship between stroke volume and ejection time was established during studies conducted by Agress et al., as described in their article, "Measurement of Stroke Volume by the Videocardiogram," *Aerospace Magazine*, December 1967).

$$SV = 0.32 * ET - 19.9 \qquad (12)$$

At a step 782, the processor 28 (FIG. 1) produces a running average of estimated stroke volume ($SV_N$) based on input signals from the cardiac wall motion sensor 22 (FIG. 1), as shown above by Equation 5, using a recursive low-pass filter to derive a digitally smoothed representation of SV.

The variable designated as $SV_N$ contains the digitally smoothed representation of the patient's stroke volume. The variable designated $SV_{N-1}$ represents the value of $SV_N$ derived using Equation 5 during the previous cardiac cycle ($SV_{N-1}$ set to be equal to $SV_T$, at the initialization step 770, until stroke volume measurements have been made).

At a step 784, the processor 28 (FIG. 1) computes a value for the variable designated as $SV_{DIFF}$, as illustrated above by Equation 6, which is the difference between $SV_T$ and $SV_N$.

At a step 786, the processor 28 (FIG. 1) multiplies this difference by a proportionality constant (K1), which is preferably −600, but may vary between −200 and −1000, to determine the required change in HR ($\Delta HR_N$). Finally, the processor 28 (FIG. 1) sums $\Delta HR_N$ with the previous value for HR ($HR_{N-1}$) at a step 788, as shown above by Equation 7 and then returns to the step 772 (to determine the affect of the new value of $HR_N$ on $SV_T$).

Figure 8:
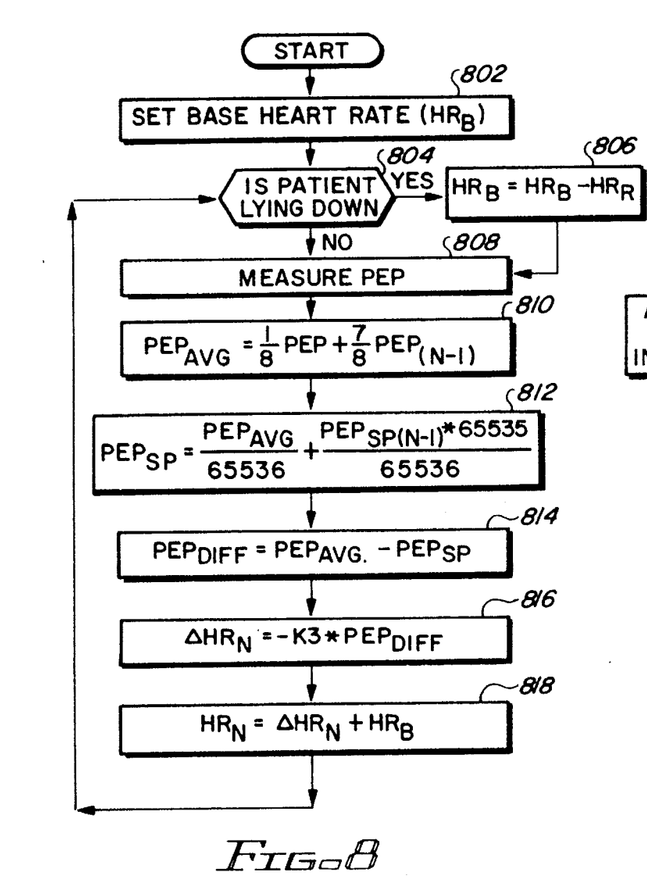
FIG. 8 is a logic flow diagram showing how the processing system of the present invention adjusts the heart rate of a patient in accordance with metabolic demands in response to changes in pre-ejection period as derived from signals from a cardiac wall motion sensor.

An embodiment of the present invention which provides hemodynamically optimal rate-responsive pacing during periods of metabolic need based on a determination of pre-ejection period is shown in FIG. 8. The control program starts when a start-up command is received from the external programmer 38 (FIG. 1) through the telemetry circuit 36 (FIG. 1).

After start-up, the processor 28 (FIG. 1) performs an initialization step 802, at which the pacemaker 20 (FIG. 1) acquires an initial base rate ($HR_B$) and other operating parameters from the external programmer 38 (FIG. 1) (which may be set by the physician) through the telemetry circuit 36 (FIG. 1), the base rate then being stored in the memory 30 (FIG. 1). The processor 28 conducts a test 804 of the position switch 46 (FIG. 1) to determine whether the patient is lying down. If the patient is supine, the processor 28 (FIG. 1) reduces the base heart rate by a predetermined amount, preferably 10 to 25 bpm (as set by the physician), at a step 806.

At a step 808, the processor 28 (FIG. 1) computes the value of the pre-ejection period (PEP) based on cardiac velocity signals for the current heartbeat, as described above in connection with FIG. 4. At a step 810, the processor 28 (FIG. 1) produces a running average of estimated pre-ejection period ($PEP_{AVG}$), as shown in Equation 13, using a recursive low-pass filter to derive a digitally smoothed representation of $PEP_{AVG}$.

$$PEP_{AVG}=(\frac{1}{8})*PEP+(\frac{7}{8})*PEP_{AVG(N-1)} \tag{13}$$

The variable designated as $PEP_{AVG}$ contains the digitally smoothed representation of the patient's pre-ejection period. At a heart rate of 60 bpm, the digital filter defined by Equation 13 has a time constant of approximately 8 seconds. The variable designated $PEP_{AVG(N-1)}$ represents the value of $PEP_{AVG}$ derived using Equation 13 during the previous cardiac cycle ($PEP_{AVG(N-1)}$ is input by the physician to be an approximate optimal value until actual measurements of PEP have been made). The processor 28 (FIG. 1) uses the computed value of $PEP_{AVG}$ to produce an eighteen-hour running average of PEP ($PEP_{SP}$) at a step 812, as shown in Equation 14.

$$PEP_{SP}=PEP_{AVG}/65536+(PEP_{SP(N-1)}*65535)/65536 \tag{14}$$

The variable designated as $PEP_{AVG}$ contains the further digitally smoothed representation of the patient's maximum cardiac wall velocity. At a pacing rate of 60 bpm, the time constant of this digital filter is approximately 18 hours. The variable designated $PEP_{SP(N-1)}$ represents the value of $PEP_{SP}$ derived using Equation 14 during the previous cardiac cycle ($PEP_{SP(N-1)}$ is initially set to an estimated value by the physician).

The processor 28 (FIG. 1) determines the difference between the two filtered representations of pre-ejection period (the 8 second representation and the 18 hour representation) at a step 814, as shown by Equation 15.

$$PEP_{DIFF}=PEP_{AVG}-PEP_{SP} \tag{15}$$

The processor 28 (FIG. 1) multiplies the computed value of $PEP_{DIFF}$ by a proportionality constant (K3), which is preferably 1 ppm/ms, but may vary between 5 and 0.3, to determine the required change in the heart rate ($\Delta HR_N$) at a step 816. Finally, the processor 18 (FIG. 1) sums $\Delta HR_N$ with $HR_B$ at a step 818, as shown by Equation 16, and then returns to the step 804.

$$HR_N=\Delta HR_N+HR_B \tag{16}$$

In addition to providing hemodynamically optimal rate-responsive pacing, as described above in connection with FIGS. 5–8, the present invention also provides hemodynamically optimal pacing therapy at rest. Rather than adjusting a single parameter, i.e., heart rate, in response to metabolic need, an alternate embodiment of the present invention varies two parameters, heart rate and AV interval, to achieve hemodynamically optimal pacing therapy. Periodically, cardiac performance is measured for various combinations of heart rate and AV interval, then the measurements are analyzed to determine whether improved cardiac performance results from changing the parameter settings.

Figure 9:
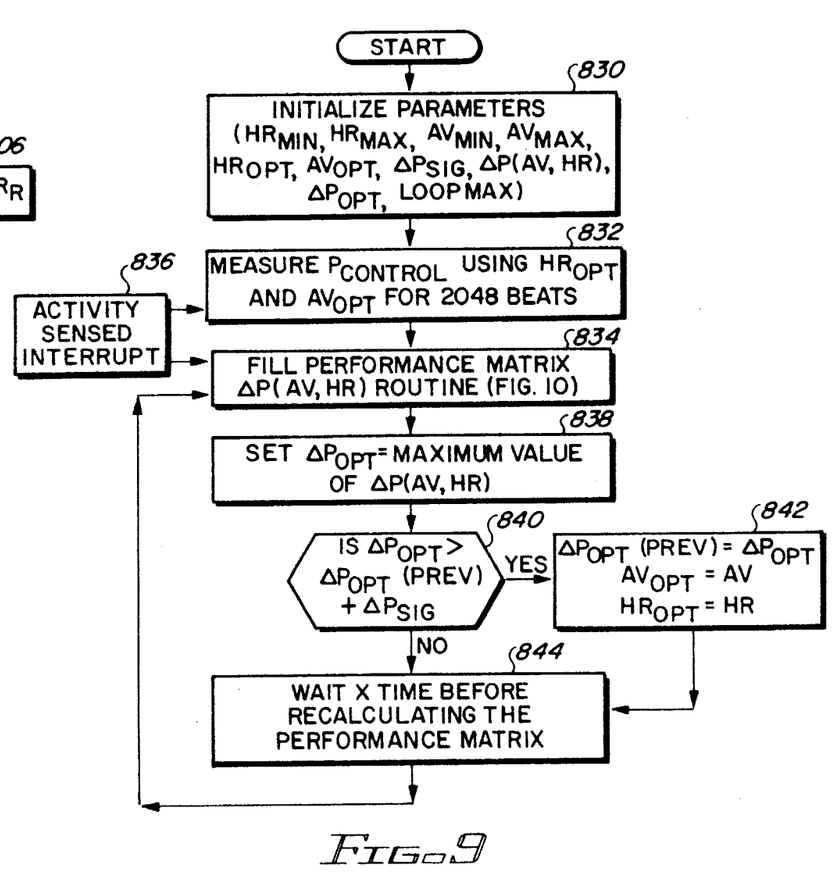
FIGS. 9 and 10 are logic flow diagrams showing how the processing system of the present invention adjusts heart rate and AV delay, for a patient at rest, in response to changes in a hemodynamic indicator as derived from signals from a cardiac wall motion sensor.

The embodiment of the present invention that provides hemodynamically optimal pacing therapy during rest is shown by a flow diagram in FIG. 9. The control program starts when a start-up command is received from the external programmer 38 (FIG. 1) through the telemetry circuit 36 (FIG. 1). This command may be sent in connection with the implantation procedure (before, during, or after), and during subsequent follow-up visits.

After start-up, the processor 28 (FIG. 1) executes a step 830 that initializes the following operating parameters based on settings from the physician: heart rate minimum ($HR_{MIN}$) (the minimum acceptable heart rate for a given patient), heart rate maximum ($HR_{MAX}$) (the maximum acceptable heart rate for a given patient), AV delay minimum ($AV_{MIN}$) (the minimum acceptable AV delay for a given patient), AV delay maximum ($AV_{MAX}$) (the maximum acceptable AV delay for a given patient), optimum heart rate ($HR_{OPT}$) (the optimal heart rate for a given patient, initially, the physician's best estimate), optimum AV delay ($AV_{OPT}$) (the optimal AV delay for a given patient, initially, the physician's best estimate), and significant cardiac performance change ($\Delta P_{SIG}$) (a threshold value representing the minimum cardiac performance improvement that must be exceeded before the optimal values will be changed).

At the step 830, the processor 28 (FIG. 1) also initializes the variables cardiac performance ($\Delta P(AV,HR)$) (a two-dimensional matrix bound by $HR_{MIN}$ and $HR_{MAX}$ and $AV_{MIN}$ and $AV_{MAX}$ which represents measured cardiac performance for each valid combination of heart rate and AV delay; initialization results in each cell of the matrix being set to zero) and optimal cardiac performance change ($\Delta P_{OPT}$) (the maximum value of measured cardiac performance; initialized to zero). Additionally, the physician sets a variable designated as LOOPMAX to be the number of times the cardiac performance matrix is updated for each optimization cycle.

At a step 832, the processor 28 (FIG. 1) establishes a control value ($P_{CONTROL}$) for hemodynamic performance based on the physician selected $HR_{OPT}$ and $AV_{OPT}$ by measuring cardiac performance for 2048 beats, summing the measured data and dividing the result by 2048. The control value is later averaged with a second measurement of cardiac performance based on the optimum parameters (the second measurement is taken after the cardiac performance is measured for a selected combination of heart rate and AV delay) so that any effects from minor variations in metabolic need are reduced.

The specific technique for measurement of cardiac performance varies depending on the desired optimization parameter. For example, optimizing cardiac performance based on stroke volume may be accomplished by averaging measured cardiac wall displacement (based on cardiac wall motion sensor signals) for a chosen heart rate and AV delay. Alternatively, optimizing cardiac performance based on relative changes in cardiac output may be achieved by taking the product of the current heart rate and stroke volume as estimated by taking the difference, 310, shown in FIG. 4. The product of this difference and the current heart rate is an estimate of the beat-to-beat cardiac output. Alternatively, stroke volume may be determined from ejection time by measuring the time from the onset of contraction to the time when cardiac velocity crosses zero using cardiac wall velocity signals. Stroke volume may also be determined by measuring pressure-time histories of arterial blood flow, or performing impedance plethysmography (where the impedance of the heart cavity is measured and the measurement is converted into stroke volume).

Instead, if optimization is based on contractility, cardiac wall velocity signals may be monitored for each heartbeat, where the maximum cardiac velocity is proportional to contractility. Additionally, pre-ejection period may be the preferred measure of hemodynamically optimal cardiac performance, in which case measurements of performance may be based on cardiac wall velocity.

Figure 10:
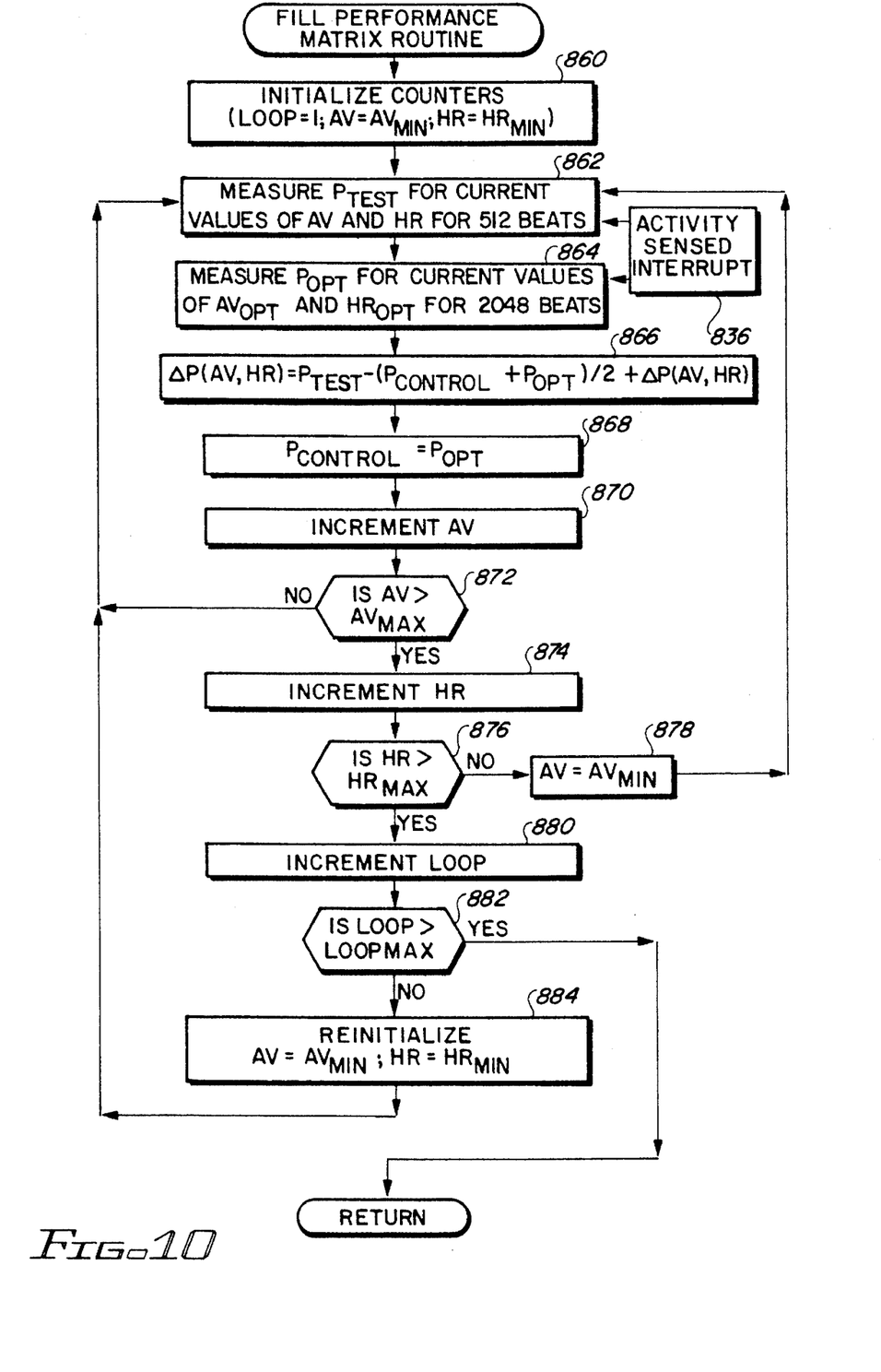

At a step 834, the processor 28 (FIG. 1) executes a subroutine for determining the cardiac performance for valid combinations of heart rate and AV delay, as shown in FIG. 10. Concurrent with the execution of the steps 832 and 834, the processor 28 (FIG. 1) executes an activity sensed interrupt step 836 which monitors the activity sensing circuit 48 (FIG. 1) to determine if the patient is undergoing activity which may cause the measured data to vary. If programmed by the physician, the processor 28 (FIG. 1) will suspend data measurement when an activity interrupt is sensed (data collection resumes when the activity level falls below a predetermined threshold). Alternatively, the physician may prefer to disable the activity interrupt because activity occurs so infrequently in relation to the time required for data collection (e.g., roughly 18 hours are required to collect a single loop of 25 cells of data (based on a five-by-five performance matrix) from a heart beating at 60 beats per minute) that variations due to activity may be inconsequential. The operation of the Fill Performance Matrix Subroutine may be better understood by referring to the graphic representation of the cardiac performance matrix shown in FIG. 11.

Figure 11:
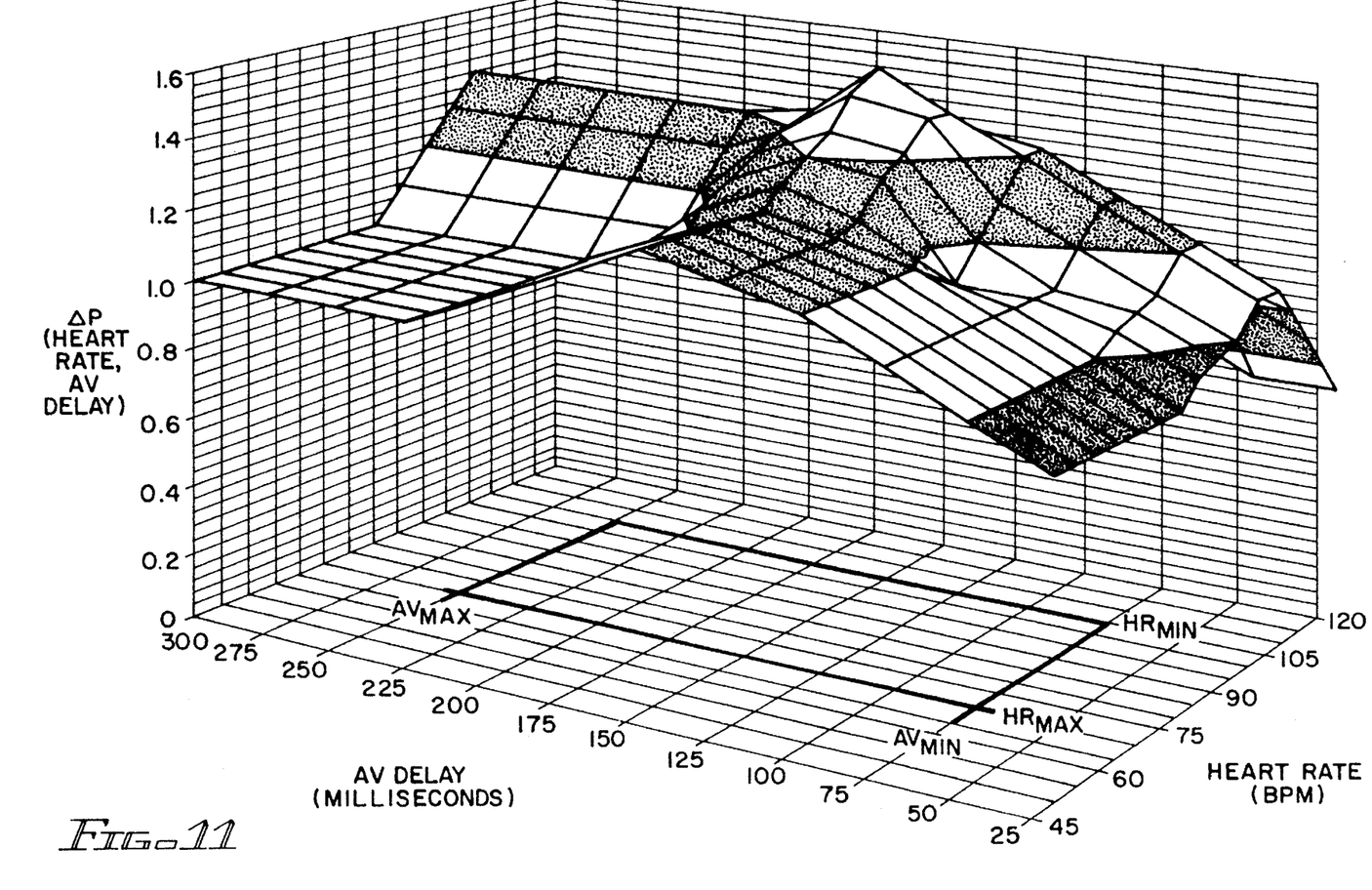
FIG. 11 is a three-dimensional graph illustrating the manner by which cardiac performance is optimized in accordance with the principles of the present invention.

FIG. 11 shows a three-dimensional representation of the cardiac performance matrix $\Delta P(AV,HR)$. A first axis is defined by AV-delay (AV), which varies from $AV_{MIN}$ of 75 milliseconds to $AV_{MAX}$ of 250 milliseconds. A second axis is defined by heart rate (HR), which varies from $HR_{MIN}$ of 65 beats per minute to $HR_{MAX}$ of 95 beats per minute. It may be practical for execution of the subroutine to index each of the values of AV and HR, for example AV may vary from 1 to 8 instead of varying from 75 to 250 by 25's. The third axis represents the value for cardiac performance for each given AV/HR pair, and is the value which is stored in each cell of the cardiac performance matrix.

For example, assume that $AV_{OPT}$ has a value equal to 175 and $HR_{OPT}$ has a value equal to 80. The processor 28 (FIG. 1) operates the Fill Performance Matrix Subroutine by measuring cardiac performance at the first cell (75, 65) for 512 beats ($P_{TEST}$). Then the processor 28 (FIG. 1) measures for 2048 beats, cardiac performance at cell (175, 80) to determine the current optimal performance ($P_{OPT}$). The value in cell (75, 65) is updated with essentially the difference between the current measured performance using the cell's parameters for AV and HR and the current performance using the optimal parameters for AV and HR. The variable AV is then incremented, in this case to 100, and the measurements are conducted again (and again for each value of AV from 125 to 250). Once each value of AV has been measured for HR equal to 65, HR is incremented to 70, AV is reset to $AV_{MIN}$, and the cycle is run again for each value of AV (from 75 to 250). After HR has been incremented beyond $HR_{MAX}$ (from 70 to 75, and so on, until HR is set to a value of 100), the variable LOOP is incremented and tested to determine whether the entire matrix needs to be updated again (as described above, the number of loops executed in a single optimization process may be set by the physician through the use of the variable LOOPMAX).

Referring again to FIG. 9, after the Fill Performance Matrix Subroutine has returned control (at the step 834), the processor 28 (FIG. 1), at a step 838, locates the cell in the cardiac performance matrix ($\Delta P(AV,HR)$) having the maximum value and sets the cardiac performance optimal change variable ($\Delta P_{OPT}$) to that maximum value. This step may be performed by incrementing the variables AV and HR from their minimum values to their maximum values until all valid combinations of AV and HR have been tested.

The processor 28 (FIG. 1), at a test 840, determines whether the new cardiac performance optimal change value ($\Delta P_{OPT}$) is greater than the sum of the previous cardiac performance optimal change value ($\Delta P_{OPT(PREV)}$) and the cardiac performance change significance value ($\Delta P_{SIG}$). If the threshold value is exceeded, the processor 28 (FIG. 1) replaces the previous cardiac performance change optimal value with the current value and replaces $AV_{OPT}$ and $HR_{OPT}$ with the values corresponding to the cell having the maximum value at a step 842. If the threshold is not exceeded, the pacemaker is providing substantially optimal pacing therapy and pacing continues at the previously selected optimal levels. At a step 844, the processor 28 (FIG. 1) suspends the optimization processing for a predetermined time period, preferably programmable for one week to one year in one-week increments (as selected by the physician), before restarting optimization data measurement again at the step 834.

Referring now to FIG. 10, the fill performance subroutine, as executed by the processor 28 (FIG. 1) is shown. The processor 28 (FIG. 1) begins the subroutine by initializing a loop counter (LOOP) and by setting the variables AV and HR equal to their respective minimum values at a step 860. At a step 862, the processor 28 (FIG. 1) measures the cardiac performance based on the present values of AV and HR for 512 beats ($P_{TEST}$) (512 beats of data are collected, summed and averaged). At a step 864, the processor 28 (FIG. 1) measures the cardiac performance using the optimal values of HR and AV ($HR_{OPT}$ and $AV_{OPT}$, respectively) for 2048 beats ($P_{OPT}$) (2048 beats of data are collected, summed and averaged). As described above in connection with FIG. 9, and specifically during the execution of steps 862 and 864, the processor 28 essentially continuously monitors the activity sensor circuit 48 (FIG. 1) to determine whether the patient is undergoing activity, in which case data measurement is temporarily suspended.

The processor 28 (FIG. 1) updates the present cell of the cardiac performance matrix (selected by the current values of HR and AV) by summing the previous value of the present cell with difference between $P_{TEST}$ and the average of $P_{CONTROL}$ and $P_{OPT}$ at a step 866, as shown by Equation 17.

$$\Delta P(AV,HR) = P_{TEST} - (P_{CONTROL} + P_{OPT})/2 + \Delta P(AV,HR) \quad (17)$$

The processor 28 (FIG. 1) replaces the current value of $P_{CONTROL}$ with the current value of $P_{OPT}$ at a step 868 before incrementing the variable AV at a step 870. The processor 28 (FIG. 1) then executes a test 872 to determine if $AV_{MAX}$ has been exceeded (due to the incrementing of AV). If $AV_{MAX}$ has not been exceeded, the processor 28 (FIG. 1) again executes the step 862. If $AV_{MAX}$ has been exceeded, the processor 28 (FIG. 1) increments the variable HR at a step 874 and executes a test 876 to determine if $HR_{MAX}$ has been exceeded. If $HR_{MAX}$ has not been exceeded, the processor 28 (FIG. 1) resets AV equal to $AV_{MIN}$ at a step 878 and again executes the step 862. If $HR_{MAX}$ has been exceeded, the processor 28 (FIG. 1) increments the variable LOOP at a step 880 and executes a test 882 to determine if LOOP exceeds LOOPMAX. If LOOPMAX has not been exceeded, the processor 28 (FIG. 1) reinitializes the variables AV and HR (to be equal to their respective minimum values) at a step 884 and again executes the step 862. If LOOPMAX has been exceeded, the processor 28 (FIG. 1) returns from the fill performance matrix subroutine (back to the step 834 of FIG. 9).

In the embodiments described above, the cardiac wall displacement signals and the cardiac wall velocity signals are derived using the sensor circuit 24 (FIG. 1) (comprising circuitry such as the circuitry described above in connection with FIGS. 2 and 3). However, therapeutic electrical stimulation may be administered equally as well by an implantable cardiac stimulating device which, instead of the sensor circuit 24 (FIG. 1), includes a processor that is programmed to derive cardiac wall displacement and cardiac wall velocity from raw acceleration signals provided by the cardiac wall motion sensor 22 (FIG. 1).

Thus, a processing system for optimizing cardiac hemodynamic performance is provided, such that during periods of patient activity, cardiac wall motion sensors are utilized, and during periods of rest, any technique for measuring cardiac performance may be utilized, including the use of cardiac wall motion sensors. One skilled in the art will appreciate that the present invention can be practiced by other than the described embodiments, which are presented for purposes of illustration and not of limitation, and the present invention is limited only by the claims which follow.

What is claimed is:

1. A rate-responsive pacemaker for providing pacing pulses to a patient's heart in accordance with metabolic need, the pacemaker comprising:

a cardiac wall motion sensor for providing signals representative of ventricular or cardiac wall motion;

a pulse generator for generating pacing pulses at a selectable rate;

a processor, coupled to the cardiac wall motion sensor and the pulse generator, for processing the cardiac wall motion sensor signals to derive physiologic parameters indicative of the patient's level of metabolic need and for selecting the rate at which the pulse generator generates pacing pulses in accordance with the derived physiologic parameters.

2. The pacemaker of claim 1, wherein the processor comprises means for processing the cardiac wall motion sensor signals to derive a physiological parameter selected from the group consisting of: stroke volume, contractility, pre-ejection period and ejection time.

3. The pacemaker of claim 2, wherein:

the cardiac wall motion sensor comprises means for measuring cardiac wall accelerations; and the signals representative of cardiac wall motion comprise cardiac wall acceleration signals.

4. The pacemaker of claim 3, wherein the processing means for deriving stroke volume comprises:

means for twice integrating the cardiac wall acceleration signals over time to derive cardiac wall displacement signals that include a maximum displacement signal and a minimum displacement signal within a heartbeat cycle; and means for measuring a difference between the maximum displacement signal and the minimum displacement signal, the difference being proportional to stroke volume.

5. The pacemaker of claim 4, wherein the processor comprises means for selecting the rate at which the pulse generator generates pacing pulses in accordance with the derived stroke volume.

6. The pacemaker of claim 3, wherein the processor derives contractility by:

integrating the cardiac wall acceleration signals over time to derive cardiac wall velocity signals that include a maximum velocity signal within a heartbeat cycle; and measuring the maximum velocity signal, the measured maximum velocity signal being indicative of contractility.

7. The pacemaker of claim 6, wherein the processor selects the rate at which the pulse generator generates pacing pulses in accordance with the signal which is indicative of contractility.

8. The pacemaker of claim 3, further comprising an IEGM sensing circuit coupled to the processor, for sensing IEGM signals, wherein the processor derives pre-ejection period by:

monitoring the IEGM signals to determine a time at which an R-wave occurs within a heartbeat cycle;

integrating the cardiac wall acceleration signals over time to derive cardiac wall velocity signals that include a maximum velocity signal within the heartbeat cycle or peak acceleration;

measuring a time at which the maximum velocity signal occurs; and measuring a time difference between the occurrence of the R-wave and the occurrence of the maximum velocity signal or peak acceleration, the time difference being representative of the pre-ejection period.

9. The pacemaker of claim 8, wherein the processor selects the rate at which the pulse generator generates pacing pulses in accordance with the measured pre-ejection period.

10. The pacemaker of claim 3, wherein the processor derives ejection time by:

integrating the cardiac wall acceleration signals over time to derive cardiac wall velocity signals that include a maximum velocity signal within a heartbeat cycle; and measuring the time at which the maximum velocity occurs, and measuring the time at which the velocity signal is equal to zero;

determining the difference between the time at which the maximum velocity occurs and the time at which the velocity signal is equal to zero, the measured difference being representative of ejection time.

11. The pacemaker of claim 10, wherein the processor selects the rate at which the pulse generator generates pacing pulses in accordance with the measured ejection time.

12. The pacemaker of claim 10, wherein processor further processes the ejection time to derive stroke volume.

13. The pacemaker of claim 12, wherein the processor selects the rate at which the pulse generator generates pacing pulses in accordance with the derived stroke volume.

14. A pacemaker for providing hemodynamically optimal pacing therapy to a patient's heart, the pacemaker comprising:

a cardiac wall motion sensor for generating signals representative of ventricular cardiac wall motion;

a pulse generator for generating pacing pulses in accordance with pacing parameters;

a processor, coupled to the cardiac wall motion sensor and the pulse generator, for processing the cardiac wall motion sensor signals to derive physiologic parameters indicative of cardiac performance and for optimally setting the pacing parameters in accordance with the physiologic parameters.

15. The pacemaker of claim 14, wherein the processor comprises means for processing the cardiac wall motion sensor signals to derive a physiological parameter selected from the group consisting of: stroke volume, contractility, pre-ejection period and ejection time.

16. The pacemaker of claim 15, wherein:

the cardiac wall motion sensor comprises means for measuring cardiac wall accelerations; and the signals representative of cardiac wall motion comprise cardiac wall acceleration signals.

17. The pacemaker of claim 16, wherein the processing means for deriving stroke volume comprises:

means for twice integrating the cardiac wall acceleration signals over time to derive cardiac wall displacement signals that include a maximum displacement signal and a minimum displacement signal within a heartbeat cycle; and means for measuring a difference between the maximum displacement signal and the minimum displacement signal, the difference being proportional to stroke volume.

18. The pacemaker of claim 17, wherein the processor comprises means for selecting the pacing parameters in accordance with the derived stroke volume.

19. The pacemaker of claim 16, wherein the processor derives contractility by:

integrating the cardiac wall acceleration signals over time to derive cardiac wall velocity signals that include a maximum velocity signal within a heartbeat cycle; and measuring the maximum velocity signal, the measured maximum velocity signal being indicative of contractility.

20. The pacemaker of claim 19, wherein the processor selects the pacing parameters in accordance with the signal which is indicative of contractility.

21. The pacemaker of claim 16, further comprising an IEGM sensing circuit coupled to the processor, for sensing IEGM signals, wherein the processor derives pre-ejection period by:

monitoring the IEGM signals to determine a time at which an R-wave occurs within a heartbeat cycle;

integrating the cardiac wall acceleration signals over time to derive cardiac wall velocity signals that include a maximum velocity signal within the heartbeat cycle or peak acceleration;

measuring a time at which the maximum velocity signal occurs; and measuring a time difference between the occurrence of the R-wave and the occurrence of the maximum velocity signal or peak acceleration, the time difference being representative of the pre-ejection period.

22. The pacemaker of claim 21, wherein the processor selects the pacing parameters in accordance with the measured pre-ejection period.

23. The pacemaker of claim 16, wherein the processor derives ejection time by:

integrating the cardiac wall acceleration signals over time to derive cardiac wall velocity signals that include a maximum velocity signal within a heartbeat cycle; and measuring the time at which the maximum velocity occurs, and measuring the time at which the velocity signal is equal to zero;

determining the difference between the time at which the maximum velocity occurs and the time at which the velocity signal is equal to zero, the measured difference being representative of ejection time.

24. The pacemaker of claim 23, wherein the processor selects the pacing parameters in accordance with the measured ejection time.

25. The pacemaker of claim 23, wherein processor further processes the ejection time to derive stroke volume.

26. The pacemaker of claim 25, wherein the processor selects the pacing parameters in accordance with the derived stroke volume.

* * * * *